(12) United States Patent
Concibido et al.

(10) Patent No.: US 10,513,743 B2
(45) Date of Patent: Dec. 24, 2019

(54) MOLECULAR MARKERS ASSOCIATED WITH CHLORIDE TOLERANT SOYBEANS

(71) Applicant: Monsanto Technology LLC, St. Louis, MO (US)

(72) Inventors: Vergel C Concibido, St. Louis, MO (US); Ivan Husic, St. Louis, MO (US); Nona Lafaver, St. Louis, MO (US); Bradley LaVallee, St. Louis, MO (US); James Narvel, St. Louis, MO (US); Jennifer Yates, St. Louis, MO (US); Xianghai Ye, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/652,926

(22) Filed: Jul. 18, 2017

(65) Prior Publication Data

US 2018/0016646 A1 Jan. 18, 2018

Related U.S. Application Data

(62) Division of application No. 14/424,454, filed as application No. PCT/US2013/056929 on Aug. 28, 2013, now abandoned.

(60) Provisional application No. 61/695,050, filed on Aug. 30, 2012.

(51) Int. Cl.
| | |
|---|---|
| *A01H 5/10* | (2018.01) |
| *C12Q 1/6895* | (2018.01) |
| *A01H 1/04* | (2006.01) |
| *C12N 15/82* | (2006.01) |

(52) U.S. Cl.
CPC .............. *C12Q 1/6895* (2013.01); *A01H 1/04* (2013.01); *C12N 15/8271* (2013.01); *C12N 15/8275* (2013.01); *C12Q 2600/13* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

2006/0135758 A1 6/2006 Wu
2010/0275286 A1* 10/2010 Wu .......................... A01H 1/02
800/260

OTHER PUBLICATIONS

Lee et al., 2004, Theor. Appl. Genet. 109: 1610-1619.*
Lee, G el al. A Major QTL Conditioning Salt Tolerance in S-100 Soybean and Descendent Cultivars. Theor Appl Genet. Sep. 9, 2004, vol. 109, No. 8, pp. 1610-1619; p. 1610, first column, first paragraph to p. 1611, second column, third paragraph; p. 1615, first column, second paragraph to p. 1616, first column, first paragraph; p. 1617, first column, second paragraph to second column, second paragraph; DOI: 10.1007/s00122-004-1783-9.
Jiang, W el al. Glycine max Diaminopimelate Epimerase mRNA, Complete Cds. Genbank Database. Jan. 1, 2010. GenBank Accession No. FJ594401, Retrieved from the Internet: <URL: hltp://www.ncbi.nlm.nih.gov/nucleotide/255671798?report=genbank&log$=nuclalign&blast_rank=2&RID=GAAYAT21013>; entire document.
Stagey. G el al. Generation of Phaseolus Vulgaris ESTs and Investigation of Their Regulation Upon Uromyces Appendiculatus Infection. BMC Plant Biology. Apr. 27, 2009, vol. 9, No. 46, Genbank Database. Apr. 1, 2008. GenBank Accession No. FE704412, Retrieved from the Internet: <URL: https://www.ncbi.nlm.nih.gov/nucest/171629305?report=est>.

* cited by examiner

*Primary Examiner* — Bratislav Stankovic
(74) *Attorney, Agent, or Firm* — James E. Davis

(57) ABSTRACT

The present invention provides methods and compositions for the identification and selection of loci modulating phenotypic expression of a chloride tolerant trait in plant breeding. In addition, methods are provided for screening germplasm entries for the performance and expression of this trait.

2 Claims, No Drawings

Specification includes a Sequence Listing.

```
                          SEQUENCE LISTING

<160> NUMBER OF SEQ ID NOS: 52

<210> SEQ ID NO 1
<211> LENGTH: 120
<212> TYPE: DNA
<213> ORGANISM: Glycine max

<400> SEQUENCE: 1
ttgtgacgga catagtcata agcttcatat tggcagggaa ggataccacg tcagcagcgc      60
tgacgtggtt tttctggctg ctatcgaaga acccgcgagt ggagaaggag attgtgaagg     120

<210> SEQ ID NO 2
<211> LENGTH: 60
<212> TYPE: DNA
<213> ORGANISM: Glycine max

<400> SEQUENCE: 2
ataaacttct ctattctaca tttcaaccgg tgaattaagc tccttctatt tcaaagtgct      60

<210> SEQ ID NO 3
<211> LENGTH: 1170
<212> TYPE: DNA
<213> ORGANISM: Glycine max
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t

<400> SEQUENCE: 3
tcgggtcagg tactccagta aagtgaaggg ttatcgcacc aatatgttcc ccatggcgac      60
ctcggaaacg agctgttatc cttcaagagt gctgcatcca cattgcacta ttccttctgt     120
caagtgtctg attttccttt tcgagcatgg caccattcag tgtaagactg cgttgtgagg     180
ttgatggaaa catgttcccg caagtctata tgattccaga tcttgtcgtt tctacgtcgc     240
cagatacacc aaagtagcat agcaaacttg atgccaattc ggtggagaga ttttgcagca     300
atttgaacac tgtatcagtc aaggttgtag cgttgttgat gtcttgcgag atctgaggca     360
agccagaatc gttgaacttg ttgacaacca aaaacacat gccacgaatt ttctagattg     420
gattggcaat actcacataa aatacagcaa tgtaccoctc tagattgaag acgttatctt     480
gttggaaggc tgttccttaa gagacgcaac ataaagtgtt taacttttgg cggaactttg     540
agttgccata acaagttcca atcaccaggg actttataat catccttgtt aatcaagttc     600
tccatcaagt agtgataacc ttagtgtgta tactccagtg ctgctgaact tccaagtcaa     660
```

```
tgaatcttgc gaattggtgt ttaggggagg tgatgcttgg atggtttgga tgtctgcgtg    720
attcacaatt tgaggaagaa tttctgtcat ccaacttcca gtggaatttc tgataacata    780
caaattaacc atctacaata atattttaaa ttaaaacaat taaatatagt aattagatat    840
ctatacgtgt tcttacttat catgctgtgt agctcagacg aatnagtttc tttctgtatt    900
ataagtaatc aaaattagat gaggaaaaca gaaacacata aaggtcttaa attgtgggga    960
aaaccagaat ttttttaatg gcattaaacc atctaaagaa ctattttaat tagaggaatg   1020
ttatgtgtga cttggtactt caacaaaatc aatgtttagc atcaactaaa agttaatgct   1080
atgtncgtcc gtgttttgat ctgataaatc tgttaatatt tatcgataaa aaaacatgtc   1140
ctgaaactaa caatggtgca aagaatcgtt                                    1170

<210> SEQ ID NO 4
<211> LENGTH: 301
<212> TYPE: DNA
<213> ORGANISM: Glycine max
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t

<400> SEQUENCE: 4
agacttgtat tcacaattaa gcaaaactga aacccaaaca cacgttaaaa ctcttgttca     60
gctcgagctt atancattan gagatcatga ccacatgtaa ctnttattat aacacacaca    120
tacacacatg agaagggatc atatttattc taggatcaaa tatacatgtg tgggaccact    180
tgaacacaaa gttatgtaga atagttgttt catgccattg ctaatcagga cttctcactg    240
ccaatctatg tgtctcattc tctctaatct ctctgtcatt ttgtgtctca ttcactagga    300
t                                                                   301

<210> SEQ ID NO 5
<211> LENGTH: 301
<212> TYPE: DNA
<213> ORGANISM: Glycine max
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t

<400> SEQUENCE: 5
tttgtgggat attcaggaaa taaaggagt caagtgtaat gaactaanat atgtgataaa      60
aactattttt ntgccaaaaa tattggtttt aaattttatt ttttatttat aagaactata    120
cttaagaagg agtttacaaa aacttacata caccactcaa acaactcagc tagatcatat    180
tgattgattt tagatttaac cataatatat atttataaaa tagaacgtgt tttctgtaaa    240
ttttaaaaat agctaagttt tcacgtcaaa tgtgtaaaat aaaatggagg ttaaagtaat    300
t                                                                   301
```

<210> SEQ ID NO 6
<211> LENGTH: 301
<212> TYPE: DNA
<213> ORGANISM: Glycine max
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t

<400> SEQUENCE: 6

```
aaaatctgta atgataaaat caataggaaa actttgaatt catatgcatt ctatgtgaaa      60
gtctaaggaa aatataaaag tttagtacgt gaatantaan aaaaatattt ataaaactca     120
gaattccaca gggatgactt actcttttga ctatcctttc aagttgtgaa ttaaattctt     180
cggatccatc aagtgagaaa tccatgtaag caattggttc ataacaaacc taatatgtac     240
ttttgacggg taatcattca aattataata aactgtaaat caaaataaat aagcaagtta     300
a                                                                    301
```

<210> SEQ ID NO 7
<211> LENGTH: 688
<212> TYPE: DNA
<213> ORGANISM: Glycine max

<400> SEQUENCE: 7

```
aaaacttcaa tcataattta ttgatttaaa tgcataaaag tgtccatcat attgacaatt      60
gtaaattggt gttaggtaat gtctttggtc aaaatatgtc catctaaata attgtttcaa     120
gtcaaaatat gccaattatg aatgtatttt cttaagtact ttatttactt ttctgcatat     180
gccatgaaaa ttgcaacaaa ttatgtacac aggttgttgc acctcgcacg ttctctttag     240
tttgttttcg gctgctgccc catcccaatt ctgcagatca tgggaataag ctaaatagtg     300
atctactcga ctcagtaaat tcaactggaa atgctttcat aacacacacg gtgtgcataa     360
attttcttag gagttttgtt cttcattcat tcattttcac tcactttctt tcccttgata     420
ataaccaata ttgtgcaggt tctatcaggg gagtacattc tacgttttgc agtaggagca     480
ccattgacag aaaggaggca tgtcaatatg gcatggcaaa ttttgcaaga taaagccact     540
gctctacttg agagtttata ggatgaatct gctctcagca tcagcaattg cttttgtgga     600
catccaatgt ttcccaagac tgcattcatt ttatgatttt ttcctctata catgattcct     660
tctttttaca ccattgtcat gtgctgta                                       688
```

<210> SEQ ID NO 8
<211> LENGTH: 806
<212> TYPE: DNA
<213> ORGANISM: Glycine max
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t

<400> SEQUENCE: 8

```
agcacaaaat ttactttttg acccatatgc taaaaataat tcattttaat ctccaatcaa      60
acatttttaa attcctttg gtccctaaca ttacacaaac tttatttttt catcctatgt     120
```

```
gtactaaatt ttatttaaag gattaacctc tctcaacata tgntttatca tatgcttgaa      180
tcaataatca aattatgatg atatatttaa atgataagat tatctactat gaatcatatg      240
ncatcttatt tggttgttta aatattatgc tcccaaaaaa taggtgctaa acatatataa      300
taaatcatat attttctaat atcttattat tatcttttct taccttagaa gatttaaata      360
gtttatcacg ccccaaacaa taaaaataaa ataaaaatcc tttattatca tgcacatgca      420
gtggccataa cacttggtcc gatgaattaa ttaaagttgg cttgcgtgct cggggatttc      480
tataagagcc ccgacaagtt tggcaaaact gggaaacaaa tggagcagtg tccgatcaca      540
attaattcaa gttgaggacc atgctcgtaa atatattctc atatgttatt atgttatgtt      600
atgtgttttt gttgacatga cacgagtagt tttttatttt tttccgttct ctgcttttg       660 ttcaaactcc aaagggtctt tctttcatct tccttccttt ctcttccatt tctataaaat      720
aatttagcca acttttttttt cttttcttcc ccctttttt caccggttct tggttctatt      780
cttagggaca aaggggaccc caagcc                                           806
```

```
<210> SEQ ID NO 9
<211> LENGTH: 301
<212> TYPE: DNA
<213> ORGANISM: Glycine max
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t

<400> SEQUENCE: 9
```

```
tgattccagg aaatttaaac atgttagcct caatataaca tcctatattg tatgttacta       60 ctactttta nacactaagt taacaaatag tttttgttcc tcaacaaaat ttcatgatta      120
aaacanagaa tatagggtgt tgtattatta gtctatgcat actaaaaata ataaaaagtg      180
agcgaaacgg tgcgtttgta acccggaaga tataaaaggc gggagagctc gagtccgagg      240
ttcaggttac ttgtttgctt gctcctcgga cacgaatgga gctgccgtta gtttagggtt      300
g                                                                     301
```

```
<210> SEQ ID NO 10
<211> LENGTH: 301
<212> TYPE: DNA
<213> ORGANISM: Glycine max

<400> SEQUENCE: 10
```

```
accacatttg ttctacatct tttccttgtg gccttcaaag ggactcacat aaacttcgta       60
gtcatcattc ttactgattc atttacttta tgataataac ttgttggtca tcattaagat      120
tttctggctc taaaaggttg gtttggcaat agatggattg tccccctttg gtcatagtgg      180 tgtaaccttaa attagtttcc atttttttata taaaaatagg ataagttgtt ctgctttatg      240
atattactca ataccgtgcc agtcattgtg gttgcatttg ggttttactg ttttttttctt      300 t                                                                     301
```

```
<210> SEQ ID NO 11
<211> LENGTH: 60
<212> TYPE: DNA
<213> ORGANISM: Glycine max
<220> FEATURE:
<221> NAME/KEY: misc_feature
```

```
<222> LOCATION: (46)..(46)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 11
gcgagttttt tttttttttt tttatgaaga catcaatatt gtgaanaatg gaatggtatn      60

<210> SEQ ID NO 12
<211> LENGTH: 301
<212> TYPE: DNA
<213> ORGANISM: Glycine max
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t

<400> SEQUENCE: 12
ttctcaagac attaacttca catgctccat aattttgacg acgctgatta ccacattcgt      60
agtccttaca actttnccta tttactatct tcaattagga ctaattttga caagtgaata     120
acatgtccgt acaaaatcta ccatgactgt gctcataaac tttaggttga tttcttggtt     180
gtggtgaccc tagcaagact atagttgaca taaatactca ctctaaaata caatcaaagc     240
tngatttatc aatcaataag aagacaaaaa gtttaagttt aataacttct ttcatcgttt     300
t                                                                     301

<210> SEQ ID NO 13
<211> LENGTH: 402
<212> TYPE: DNA
<213> ORGANISM: Glycine max

<400> SEQUENCE: 13
cagcaactcc tcgaggccaa gcgaaggcag aggaggtcca atcagaagct tgtattcgat      60
tgtgtgaatg tctcactaat agaaattact ggttatggat cagagaagaa ttacttgatg     120
ggtagtaggt tgtgcagtgg gagccacagc agggtccaag tcccagaagc tgcatctccc     180
ccattggtgg acctcattgt ggcacagatg aaggagttaa tatctagtgc tatgagttct     240
gtttgggtgg tggattgtgg ggacagtaac agcctggtgg tagagagtgt tgtcagaaaa     300
gaggttgtgg gcaaagggtg ggttgagctt atgggattgg agatggatat tttggtgaag     360
gaagtagagg ggaagctgct agaagaactt gtggaggatg cg                        402

<210> SEQ ID NO 14
<211> LENGTH: 301
<212> TYPE: DNA
<213> ORGANISM: Glycine max
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t

<400> SEQUENCE: 14
ccaatgatgc aaacctagga tttcactact atagttccaa catttggaag aagggaataa      60
```

```
tagtgctaac ataactaagc tcatgtcaat tagtactatn agaatcatgc tggtgctggc    120
cacagttgtt gtggcaataa ttgtggttgt tccaaagaga gtaaaagcag ttcgagcgtt    180
ctttgtgttt ggggactcac tggttgacag tggcaacaac aattacttgc caaccatcag    240
tacaaattaa ttttatcaca atttaatctt catcntcatt cctatataat ttttttttaac   300 a                                                                    301
```

<210> SEQ ID NO 15
<211> LENGTH: 121
<212> TYPE: DNA
<213> ORGANISM: Glycine max

<400> SEQUENCE: 15

```
ccacaagttc ttctagcagc ttccctctca cttccttcac caaaatatcc atctccaatc    60
tcataagctc aacccaccct ttgcccacaa cctcttttct gacaacactc tctaccacca   120
g                                                                   121
```

<210> SEQ ID NO 16
<211> LENGTH: 301
<212> TYPE: DNA
<213> ORGANISM: Glycine max

<400> SEQUENCE: 16

```
tcagtgacaa attgaatttt taagaactta attgtgtgat taaattctttt taaaaactga    60 tatgacaagt gtaacatttt tagaagatta aatttaggga ttttttcaaag tttttagtac   120 agtaattatg tcggaatcta agttttttttt ccctctgggg gagagggata tcttaaatgt   180
tagtgttaac ttcaacattc ctgcgggtcc acctaaaagt aattggtttc ataatagacc    240
tcatcttatc cttcattgtc ggacctgcat catcacagta ccagaagaaa gtaaccatct    300
t                                                                   301
```

<210> SEQ ID NO 17
<211> LENGTH: 60
<212> TYPE: DNA
<213> ORGANISM: Glycine max

<400> SEQUENCE: 17

```
ctagccactc cctatctttc tctctcctct tctgaatttg acggttgcac cgcgtaatct    60
```

<210> SEQ ID NO 18
<211> LENGTH: 301
<212> TYPE: DNA
<213> ORGANISM: Glycine max
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 18

```
taaaagggaa agaacgtttg cagttgtgga atatctttac ttgaaggatg tttgtggtga    60
```

```
tcttttatga atatggtgtt ggnttttntt tgttgacgtt gattcaacan aagccatagt    120
taactgagcc atggcattaa aagattatca caattagaca ataaaaagga aaattaaatg    180
ctggtaggac cattaactnc agccgtttca gcaatagagg cgcagttttt aggatcctag    240
ttctactaaa ttgtgggcag ggggtgactt aaacattatt gcactttta aactaaattg     300 a                                                                   301
```

```
<210> SEQ ID NO 19
<211> LENGTH: 301
<212> TYPE: DNA
<213> ORGANISM: Glycine max
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 19
```

```
aaagtncttc aaatggtatt gcagataaat aaataaataa ctttgtatac tattattgtg    60
gatggtttct tttagtccca accgcnaata tctttcattg tgacaccata ctcttccttt    120
taaatttttt gggttcattg taggtgcaaa gagctaacct aagaagttaa ggtcgtcact    180
tgtgcgccat taataataga atctatgaag attcaactaa tgcaatata gaaaggaatg     240 aaattgtttt taagtagtgt tgcatgttca taaatttcgt tctatctaat ctattattta    300
c                                                                   301
```

```
<210> SEQ ID NO 20
<211> LENGTH: 301
<212> TYPE: DNA
<213> ORGANISM: Glycine max
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 20
```

```
ttaacacata aatcgaagga cctacnagaa agataaaaga taaagatct ctaaataaaa     60 aattntctca tttcttaaat atattatnaa attatgtttg ttaacnaaaa caaacacaaa    120
tttcacgatt aacaatcatg ttttatttt aattttaat taattaatat aatatataat     180
tgatataaaa aatagaaaaa agtgtactac gtgacattgg aaagatcacc ctgtacatac    240
tcgagagtca agacttaact acttcatgat gatgtagcaa aaacaatcct attttaatag    300
a                                                                   301
```

```
<210> SEQ ID NO 21
<211> LENGTH: 301
<212> TYPE: DNA
```

```
<213> ORGANISM: Glycine max
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t

<400> SEQUENCE: 21
gtcttggcat ggtgtttgca attccatggc ttttatgtat cgtattaatt aacgagatac     60
gataggcatt ggtatttggt ggctatagcc accgtgattt ctagtttaat ttgccgaact    120
ttatatttat aatctgctan atgccaaccg ggtgaggata agagagtacg aatcgtttat    180
ctaaattgca tcagcagtag acgaagctgc ttgtgaagtt tctcaatcgc aaaaataata    240
ctaaacatac actttattca tcaattaacg gtcgatcaat antaaacaga tcatccaagc    300
a                                                                    301

<210> SEQ ID NO 22
<211> LENGTH: 301
<212> TYPE: DNA
<213> ORGANISM: Glycine max
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 22
ttgagnccag catccttggg attgggaaca tctctggcnc ttgtagccac agccagagca     60
agaaccaaca ccaacataca ccacttagcc atgtctctct ttgtctccca cacacttgga    120
ctctccttaa tttagttagt tactctgttt agtgactgtg tcgtgtggag agagtgcttt    180
ttataggggg gaaacataaa ctaaccggtg aagggcagtt ggcaatggta aatgaaactt    240
taatgtcatt gcagactgca gagccaggag ttgggtcgat cttgatcgat atatcttctt    300
c                                                                    301

<210> SEQ ID NO 23
<211> LENGTH: 301
<212> TYPE: DNA
<213> ORGANISM: Glycine max
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t

<400> SEQUENCE: 23
aaaagcctct catagtccat tcctgngtta tctcgaattc tagatagnta acgtgtaatg     60
gataaacata tatcatttcc ttttatttttt tcttgaggta gtctaagact aagacctggt    120
cctcatgtag ggaagactga agagagactg agcgtaaaac aatttcggta agattcgaga    180
acttatcaga ggacatggtg tcttttttatc attttgtttt ttaaacttat agttaagaga    240
gacacaggtt gggttgggtc aagtttagtt agcttcaaac caaacttaat agtttaatca    300
a                                                                    301
```

<210> SEQ ID NO 24
<211> LENGTH: 121
<212> TYPE: DNA
<213> ORGANISM: Glycine max

<400> SEQUENCE: 24
tgcgattaaa atccaattaa aaaagcataa agtaaaataa gttttttaaaa caggtatctg      60 aaggaaagca actacattta gtccacttcc tcaatcttgg ggccagcacc acttccacca     120
g                                                                     121

<210> SEQ ID NO 25
<211> LENGTH: 301
<212> TYPE: DNA
<213> ORGANISM: Glycine max
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t

<400> SEQUENCE: 25
tgagaaacta gataaatctc catatgttat gtcattttgt aaaatattgc taatttacta      60
actttatntt tatttcttgc aancaacaac ctaacaggaa tgattctcca atnttttctt     120
gccaccaaat ctaactcccc aaatgcgaat ttagtcttta agttgattaa cttnatcttg     180
ttcctctttt acaacctcat tcagatgtcc ctattaatta cctctaaagg gagttaagct     240
aaagtaggcc ctaagagaaa acccttttcc aggggaaacc aatattccaa caaagaggag     300
g                                                                     301

<210> SEQ ID NO 26
<211> LENGTH: 301
<212> TYPE: DNA
<213> ORGANISM: Glycine max
<220> FEATURE:
<221> NAME/KEY: misc_feature
<222> LOCATION: (169)..(169)
<223> OTHER INFORMATION: n is a, c, g, or t

<400> SEQUENCE: 26
tatttattta cttgaaaaac aatgtagtat atgggaatag ttggtcgttg ttttttcaaca     60 cgtttcctgt gagattgttg tcttttttgg cttctgaaag tgaatggtaa ataaatgctc    120
tgtcaactag agttgtacat gcatgtatta attagttttt gaaatatana tttaacttga    180
tttcctgtca actatatatc aatcttatcc aatctgttaa caaccactgt aaaatgaagt    240
tttgatggtt tgaattcatc tttcaaattt tcaaatgaag attttaatga tagatttgaa    300
t                                                                     301

<210> SEQ ID NO 27
<211> LENGTH: 301
<212> TYPE: DNA

<213> ORGANISM: Glycine max
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 27

```
ttatattgcc cttccacaaa aggngggag gggaagatga agaggtgaca gaagacttag      60
ggcagggttn gagggaagtc aatcaaaggg tgcttcaaaa tgcagcctgc tctgtcgcag    120
tgctagtcaa tcgtggggtt gccagaaggt acgaacaaga acctgagaca agtgttgctg    180
caaggaaaag agtgtgcata attttcattg gtgaccaca tgatcgcaag gttttggagt     240
taggtagcag aatggcagag catccagcaa ttaggttgct tttagtgaga ttcacttcat    300
a                                                                    301
```

<210> SEQ ID NO 28
<211> LENGTH: 301
<212> TYPE: DNA
<213> ORGANISM: Glycine max

<400> SEQUENCE: 28

```
aaaagtattt ttttctcat ttttattcaa attatgagac atttaaaaca caatcatagt      60
ctttatcaaa tatatgactt atagatgaaa tttaatttgt acttttcaaa ctaaagttac    120
cctgttaaaa ctcggtttgt attttaact aaacaggccc ttagtcactc aagtcgaagg     180
accattttgc gaaatggaaa attttctgc tccatgcatt cttttcttgt gcgtataacc     240
attctgcttt gttccattgc atcctattcc tgtgtaattt ccaatataga agtaacagaa    300
a                                                                    301
```

<210> SEQ ID NO 29
<211> LENGTH: 301
<212> TYPE: DNA
<213> ORGANISM: Glycine max
<220> FEATURE:
<221> NAME/KEY: misc_feature
<222> LOCATION: (137)..(137)
<223> OTHER INFORMATION: n is a, c, g, or t

<400> SEQUENCE: 29

```
tgcgggggct agatataagg tgggtttagt ggtaaagggt gaaggaaggg agggataggt      60
cgtgggtttg aattccccg catgaatttg atccttacat ttctacaagt cagagaaatt    120
ggtccctctc ctcacantgt atgcattgtt tgttgacgtg gccagtcaca tggcatctgg    180
gaccaaaaca aactagattt aaaaaatgca aggactaaat ttatcgattt taaaatacag    240
agggtgtgtt tttggattgg tggtgagttg aagtcaccat gaattttaga ggctaacaaa    300
c                                                                    301
```

<210> SEQ ID NO 30
<211> LENGTH: 384
<212> TYPE: DNA
<213> ORGANISM: Glycine max

<400> SEQUENCE: 30

```
cattttttct ccgatcccct attcctctcc attctccgtt gtgtcgattt ttgttactca      60
aaagggaaat tgatttgata gatagacaga tagatcgttt ctatgggtta aagtgaaatc    120
```

```
cgaatccgaa tctgaatctg aatctgatcc aatcattttc atgttagggc gtgcgatctc      180
caatcaagcg cggttgtgtt taggtttcat tttgttgggc gtgtgagtcg taggggtttt      240
cgaagagcat agaataatgc cttcggtgcc cgttgatctc cgtctagttc cttctttgac      300
cgttttccat ggtggatcct cttttcatcg tctgaaaaat cttgaaaaaa gtgatcggcg      360
tggtaatctt agttaacaat aaca                                              384
```

<210> SEQ ID NO 31
<211> LENGTH: 365
<212> TYPE: DNA
<213> ORGANISM: Glycine max

<400> SEQUENCE: 31

```
cgtcgcgatt ggctaggtat aacaagaagc ctaccattac ttccagggag atccaaacgg       60
cggtgcgttt ggtcctccct ggggagttgg ccaaacacgc tgtctctgaa ggtaccaagg      120
ccgtcaccaa gttcaccagc tcttgattgg ttttgtttcc tgtgtttcga ttagggtttt      180
ctgttgaccc cgatttgatt cgcattttta aattagggtt ttattttcct ttttgttgct      240
tttgagggtg tagatgtaaa attaaagctt tattttttaaa taatataaat gccgtttttt      300
aatatgcctt gttttgaatt gtgatccgat cgaaacgtct ttttgcgtct tctttggttt      360
tctgg                                                                   365
```

<210> SEQ ID NO 32
<211> LENGTH: 301
<212> TYPE: DNA
<213> ORGANISM: Glycine max

<400> SEQUENCE: 32

```
tttaattaat agagtaagag tatgaatttg tcataaacct aaacctcttc aactttatg       60 aatgaaagaa aaatatcaat accatgacgg cgtttctgac ggtcgagcat tgtaactgag      120
atattctgtt aggtttggag agtagttttg tttagtttgg tgtcaaaata tagaaagaga      180
atattctttt taattggtcc agagcaaaat ggatattgga caatggacat agtcaggatc      240
aggtgtggca acgttctca gttgacagtt gtctagtcta atcctgaatt cgcttgttga      300
t                                                                       301
```

<210> SEQ ID NO 33
<211> LENGTH: 301
<212> TYPE: DNA
<213> ORGANISM: Glycine max
<220> FEATURE:
<221> NAME/KEY: misc_feature
<222> LOCATION: (147)..(147)
<223> OTHER INFORMATION: n is a, c, g, or t

<400> SEQUENCE: 33

```
cctacagcaa ttagagagtg ggggttcact tgttctataa ctgttcattg ccttatttgg       60
taatattgtt ttgatcgtta tatacaatta attctatcac aaaattgact gaatgaaatc      120
ctaaccattc aaaataaaat atttttnaaa aaattagacc ctatatatga ttgtggtgac      180
tgtagtagga ccatgtattt ccattttcta acggtagtag gaaaatcata gtccctcttt      240
atccatccca atttcacttc atatttcttt ttattttaca tcacattatt tatcacatct      300
a                                                                       301
```

<210> SEQ ID NO 34

```
<211> LENGTH: 301
<212> TYPE: DNA
<213> ORGANISM: Glycine max

<400> SEQUENCE: 34
ctacttttca tctttcttaa gttaatatga atttaagagt tggggttttt ttgaattatg      60
atcctgtatg tttttacaag catcttctcg ataatgtgaa ttgatagaat aattattttc     120
ttcttagaaa tgaaatcttt atattctgga aagttaatag gagctgtgag ttatagtaaa     180
agttattatt gatgtcgtta tgcttccttc tcaactttgg ataattgggc cttagttgag     240
cttaggttga tccaggagcg gaataccttg taatcttgta tgtacaacat tttggagttt     300
t                                                                    301

<210> SEQ ID NO 35
<211> LENGTH: 60
<212> TYPE: DNA
<213> ORGANISM: Glycine max

<400> SEQUENCE: 35
gacgagatgg acggttatag tccaaaatgg tttcataaag cgaagccatt cataggtgtt      60

<210> SEQ ID NO 36
<211> LENGTH: 60
<212> TYPE: DNA
<213> ORGANISM: Glycine max

<400> SEQUENCE: 36
ccatttcgcc aagtaccacg gcctcggaaa cgacttcgtt ttgattgaca acagagactc      60

<210> SEQ ID NO 37
<211> LENGTH: 21
<212> TYPE: DNA
<213> ORGANISM: Glycine max

<400> SEQUENCE: 37
agcatggcac cattcagtgt a                                                21

<210> SEQ ID NO 38
<211> LENGTH: 25
<212> TYPE: DNA
<213> ORGANISM: Glycine max

<400> SEQUENCE: 38
ggaatcatat agacttgcgg gaaca                                            25

<210> SEQ ID NO 39
<211> LENGTH: 18
<212> TYPE: DNA
<213> ORGANISM: Glycine max

<400> SEQUENCE: 39
aacctcacaa tgcagtct                                                    18

<210> SEQ ID NO 40
<211> LENGTH: 16
<212> TYPE: DNA
<213> ORGANISM: Glycine max

<400> SEQUENCE: 40
cctcacaacg cagtct                                                      16
```

```
<210> SEQ ID NO 41
<211> LENGTH: 24
<212> TYPE: DNA
<213> ORGANISM: Glycine max

<400> SEQUENCE: 41
ctcccaaaaa ataggtgcta aaca                                            24

<210> SEQ ID NO 42
<211> LENGTH: 28
<212> TYPE: DNA
<213> ORGANISM: Glycine max

<400> SEQUENCE: 42
gcatgtgcat gataataaag gattttta                                        28

<210> SEQ ID NO 43
<211> LENGTH: 15
<212> TYPE: DNA
<213> ORGANISM: Glycine max

<400> SEQUENCE: 43
ccccaaaaaa taaaa                                                      15

<210> SEQ ID NO 44
<211> LENGTH: 15
<212> TYPE: DNA
<213> ORGANISM: Glycine max

<400> SEQUENCE: 44
cccaaacaat aaaaa                                                      15

<210> SEQ ID NO 45
<211> LENGTH: 34
<212> TYPE: DNA
<213> ORGANISM: Glycine max

<400> SEQUENCE: 45
gtgtgaatgt ctcactaata gaaattactg gtta                                 34

<210> SEQ ID NO 46
<211> LENGTH: 16
<212> TYPE: DNA
<213> ORGANISM: Glycine max

<400> SEQUENCE: 46
cctgctgtgg ctccca                                                     16

<210> SEQ ID NO 47
<211> LENGTH: 20
<212> TYPE: DNA
<213> ORGANISM: Glycine max

<400> SEQUENCE: 47
ttgatgggta gtaggttgtg                                                 20

<210> SEQ ID NO 48
<211> LENGTH: 20
<212> TYPE: DNA
<213> ORGANISM: Glycine max

<400> SEQUENCE: 48
ttgatgggta gtatgttgtg                                                 20
```

```
<210> SEQ ID NO 49
<211> LENGTH: 19
<212> TYPE: DNA
<213> ORGANISM: Glycine max

<400> SEQUENCE: 49
aggccgtcac caagttcac                                            19

<210> SEQ ID NO 50
<211> LENGTH: 26
<212> TYPE: DNA
<213> ORGANISM: Glycine max

<400> SEQUENCE: 50
agaaaaccct aatcgaaaca caggaa                                    26

<210> SEQ ID NO 51
<211> LENGTH: 18
<212> TYPE: DNA
<213> ORGANISM: Glycine max

<400> SEQUENCE: 51
agctcttgat tggttttg                                             18

<210> SEQ ID NO 52
<211> LENGTH: 18
<212> TYPE: DNA
<213> ORGANISM: Glycine max

<400> SEQUENCE: 52
agctcttgat tcgttttg                                             18
```

MOLECULAR MARKERS ASSOCIATED WITH CHLORIDE TOLERANT SOYBEANS

CROSS REFERENCE TO RELATED APPLICATIONS

This application is a divisional of U.S. patent application Ser. No. 14/424,454, filed Feb. 27, 2015, which is the U.S. National Stage filing of International Application No. PCT/US2013/056929, filed Aug. 28, 2013, which claims benefit of and priority to U.S. Provisional Application No. 61/695,050 filed on 30 Aug. 2012, which are incorporated herein by reference.

INCORPORATION OF SEQUENCE LISTING

A sequence listing containing the file named "46_21_58552.txt" which is 23,173 bytes (measured in MS-Windows®) and created on Aug. 26, 2013, comprises 52 nucleotide sequences, is provided herewith via the USPTO's EFS system and is herein incorporated by reference in its entirety.

BACKGROUND OF INVENTION

Deployment of chloride tolerant cultivars is an effective approach to minimize yield loss in a saline soil. In soybean, *Glycine max* (L.) Merr., substantial genetic variation exists for a response to salt stress. However, breeding for chloride tolerance is hampered because no economically viable screening method has been developed for practical breeding.

Salt stress can lead to symptoms such as stunted growth, reduced yield and death in sensitive soybean species. As agricultural land is increasingly salinized through inefficient fertilizer practices, chloride-water intrusion, and use of poor quality irrigation water, development of chloride tolerant cultivars becomes increasingly important as a means of combating salt-related yield losses.

In soybean, the salinity stress inhibits seed germination and seedling growth, reduces nodulation, and decreases biomass accumulation and seed yield. Previous studies identified the Ncl gene on linkage group N, which confers tolerance to the plant through chloride exclusion; not allowing Cl(−) to translocate from the roots into the rest of the plant where it can accumulate and become toxic. However, the markers available to identify this gene are not predictive and do not translate well from the laboratory to the field. As many as 20% of soybean cultivars released for the southern USA have economic levels of chloride tolerance, but no economically viable screening method for chloride tolerance has been developed for practical breeding use. Marker assisted breeding has been proposed to accelerate the development of chloride tolerant cultivars; however, there are few commercial examples of successful marker-assisted breeding for tolerance to chloride, or other abiotic stresses, in soybean.

For these reasons, chloride tolerance may be a particularly good candidate for adaptation to marker-assisted breeding. A prerequisite for such a breeding effort is knowledge of the genomic location of the major gene for chloride tolerance in soybean.

SUMMARY OF INVENTION

Provided herein are soybean plants comprising an introgressed genomic region associated with a chloride tolerant phenotype. Also provided herein are markers that reside outside of a genomic region associated with a chloride tolerant phenotype and that facilitate breeding activities that include, but are not limited to, introgression of this genomic region. Markers and specific alleles thereof that are associated with a chloride tolerant phenotype are also provided. Methods of obtaining a soybean plant that exhibits a chloride tolerant phenotype and methods of obtaining a soybean plant comprising in its genome at least one chloride tolerant locus are also provided. Methods of introgressing one or more genomic regions associated with a chloride tolerant phenotype into soybean germplasm that lacks the one or more genomic region associated with a chloride tolerant phenotype are provided. Identification of molecular markers associated with loci that confer the chloride tolerant phenotype has significant economic value. By using markers associated with the chloride tolerant trait, breeders can select soybean varieties with the favorable alleles (i.e. alleles that are associated with the chloride tolerant trait) for use in trait integration. They can also use the markers to help them eliminate unfavorable alleles (i.e. alleles that are not associated with the chloride tolerant trait) in soybean. This invention provides for commercially desirable transgenic soybean lines that carry a genomic region that is associated with a "chloride tolerant" phenotype and tolerate high dosages of glyphosate.

Methods of identifying a soybean plant that comprises a genotype associated with a chloride tolerant phenotype are thus provided. In certain embodiments, methods of identifying a soybean plant that comprises a genotype associated with a chloride tolerant phenotype comprise: detecting in the soybean plant an allele in at least one chloride tolerant marker locus associated with the chloride tolerant phenotype. In various embodiments, the chloride tolerant marker locus is in a genomic region flanked by loci FE704412 (SEQ ID NO: 1) and AW760852 (SEQ ID NO: 36), and denotes that the plant comprises a genotype associated with a chloride tolerant phenotype. In certain embodiments, the methods further comprise the step of selecting the denoted plant from a population of plants. In certain embodiments of any one of the aforementioned methods, the denoted plant comprises a transgene that confers tolerance to glyphosate. In certain embodiments of the aforementioned methods, a plant that exhibits a chloride tolerant phenotype is selected. In certain embodiments of the aforementioned methods, the genotype associated with a chloride tolerant phenotype comprises at least one polymorphic allele of at least one marker in a first sub-region of the chromosome 3 region that is flanked by loci BI972982 (SEQ ID NO: 2) and BI699634 (SEQ ID NO: 17) and/or at least one polymorphic allele of at least one marker in a second sub-region of the chromosome 3 region that is flanked by loci BG047538 (SEQ ID NO: 11) and AW719859 (SEQ ID NO: 35). In certain embodiments of the aforementioned methods, the genotype associated with a chloride tolerant phenotype comprises at least one polymorphic allele of at least one marker in the chromosome 3 region selected from the group consisting of NS0124217 (SEQ ID NO: 3), NS0096117 (SEQ ID NO:8), NS0205902 (SEQ ID NO: 13), and NS0203171 (SEQ ID NO: 31) that is associated with a chloride tolerant phenotype.

Also provided are methods for obtaining a soybean plant comprising in its genome at least one chloride tolerant locus. In certain embodiments, the method comprises the steps of: a) genotyping a plurality of soybean plants with respect to at least one chloride tolerant locus in a first chromosome 3 genomic region flanked by loci FE704412 (SEQ ID NO: 1) and AW760852 (SEQ ID NO: 36); and, b) selecting a soybean plant comprising in its genome at least one chloride tolerant locus comprising a genotype associated with chloride tolerant phenotype. In certain embodiments of these methods, the genotype associated with a chloride tolerant phenotype comprises at least one polymorphic allele of at least one marker in a first sub-region of the chromosome 3 region that is flanked by loci BI1972982 (SEQ ID NO: 2) and BI699634 (SEQ ID NO: 17); and/or at least one polymorphic allele of at least one marker in a second sub-region of the chromosome 3 region that is flanked by loci BG047538 (SEQ ID NO: 11) and AW719859 (SEQ ID NO: 35). In certain embodiments of the aforementioned methods, the genotype associated with a chloride tolerant phenotype comprises at least one polymorphic allele of at least one marker in the first chromosome 3 region, the first sub-region, or the second sub-region, wherein the marker is selected from the group consisting of NS0124217 (SEQ ID NO: 3), NS0096117 (SEQ ID NO:8), NS0205902 (SEQ ID NO: 13), and NS0203171 (SEQ ID NO: 31). In certain embodiments, the plurality of soybean plants comprises a population that is obtained by: i) crossing a parent plant comprising at least one chloride tolerant locus with a parent plant comprising at least one chloride tolerant locus; or, ii) obtaining seed or progeny from a parental plant segregating for at least one chloride tolerant locus. In certain embodiments, the plurality of soybean plants comprises a population that is obtained by: i) crossing a parent plant comprising at least one chloride tolerant locus with a parent plant that lacks the one or more genomic region associated with a chloride tolerant phenotype; or, ii) obtaining seed or progeny from a parental plant segregating for at least one chloride tolerant locus. In certain embodiments, the population contains plants that comprise a transgene that confers tolerance to glyphosate. In certain embodiments, the aforementioned methods can further comprise the step of assaying for the presence of at least one additional marker, wherein the additional marker is either linked or unlinked to the chromosome 8 genomic region. In certain embodiments of the aforementioned methods, the plurality of soybean plants, the soybean plant, and/or progeny thereof comprising one or more chloride tolerant locus and a transgene that confers tolerance to glyphosate are exposed to a dosage of glyphosate sufficient to cause detrimental effects in a plant that does not confer tolerance to glyphosate. In certain embodiments of the aforementioned methods, a plant that exhibits a chloride tolerant phenotype is selected.

Also provided herein are methods for producing a soybean plant comprising in its genome at least one introgressed chloride tolerant locus. In certain embodiments, the method comprises the steps of: a) crossing a first chloride tolerant soybean plant with a second soybean plant comprising: a chloride tolerant locus in a first chromosome 3 genomic region flanked by loci FE704412 (SEQ ID NO: 1) and AW760852 (SEQ ID NO: 36), and at least one linked polymorphic locus not present in the first chloride tolerant soybean plant to obtain a population segregating for the chloride tolerant loci and the linked polymorphic locus; b) detecting at least two polymorphic nucleic acids in at least one soybean plant from the population, wherein at least one of the polymorphic nucleic acids is located in the first chromosome 3 region and wherein at least one of the polymorphic amino acids is a linked polymorphic locus not present in the first chloride tolerant soybean plant; and c) selecting a soybean plant comprising a genotype associated with a chloride tolerant phenotype and at least one linked marker found in the second soybean plant comprising a chloride tolerant locus but not in the first chloride tolerant soybean plant, thereby obtaining a soybean plant comprising in its genome at least one introgressed chloride tolerant locus. In certain embodiments of the methods, at least one of the first or the second soybean plants comprises a transgene that confers tolerance to glyphosate. In certain embodiments, the chloride tolerant locus comprises at least one polymorphic allele of at least one marker in a first sub-region of the chromosome 3 region that is flanked by loci BI972982 (SEQ ID NO: 2) and BI699634 (SEQ ID NO: 17); and/or at least one polymorphic allele of at least one marker in a second sub-region of the chromosome 3 region that is flanked by loci BG047538 (SEQ ID NO: 11) and AW719859 (SEQ ID NO: 35). In certain embodiments of the aforementioned methods, the polymorphic nucleic acid detected in step (b) is detected with at least one marker selected from the group consisting of NS0124217 (SEQ ID NO: 3), NS0096117 (SEQ ID NO:8), NS0205902 (SEQ ID NO: 13), and NS0203171 (SEQ ID NO: 31). In certain embodiments of the aforementioned methods, the linked polymorphic locus is detected with a genotypic marker, a phenotypic marker, or both. In certain embodiments of the methods, the linked polymorphic locus is detected with a marker that is located within about 1000, 500, 100, 40, 20, 10, or 5 kilobases (Kb) of the chloride tolerant locus. In certain embodiments, the linked polymorphic locus is detected by at least one marker selected from the group consisting of NS0124217 (SEQ ID NO: 3), NS0096117 (SEQ ID NO:8), NS0205902 (SEQ ID NO: 13), and NS0203171 (SEQ ID NO: 31). Also provided herein are soybean plants comprising an introgressed chloride tolerant locus made by the aforementioned methods. In certain embodiments, a soybean plant comprises an introgressed chloride tolerant locus and one or more polymorphic loci comprising alleles or combinations of alleles that are not found in a chloride tolerant soybean variety and that are linked to the introgressed chloride tolerant locus, wherein the plant is produced by the aforementioned methods. Also provided herein are soybean plants comprising an introgressed chloride tolerant locus and a transgene that confers tolerance to glyphosate, made by the aforementioned methods.

Also provided are soybean plants comprising an introgressed chloride tolerant locus and one or more polymorphic loci comprising alleles or combinations of alleles that are not found in a chloride tolerant soybean variety and that are linked to the introgressed chloride tolerant locus.

In certain embodiments, methods for obtaining a soybean plant that exhibits a chloride tolerant phenotype are described. The methods comprise the steps of: a) crossing a soybean plant that exhibits a chloride tolerant phenotype with a soybean plant that exhibits a chloride tolerant phenotype, wherein at least one of the soybean plants comprises a transgene that confers tolerance to glyphosate, and b) selecting a progeny plant from the cross, wherein the progeny plant comprises the transgene that confers glyphosate tolerance and wherein the progeny plant exhibits a chloride tolerant phenotype are provided. In certain embodiments of the methods, the selection in step b can comprise: i) genotyping the progeny plant with respect to a chloride tolerant locus in a chromosome 3 genomic region flanked by FE704412 (SEQ ID NO: 1) and AW760852 (SEQ ID NO: 36); and/or ii) exposing the progeny plant to glyphosate and scoring the plant for a chloride tolerant phenotype. In certain embodiments of the methods, a soybean plant that exhibits a chloride tolerant phenotype comprises at least one linked or unlinked marker not present in the first chloride tolerant soybean plant. In certain embodiments, the progeny plant is further selected for the presence of the linked or unlinked marker.

Also provided are methods of breeding soybean plants. The methods comprise the steps of: a) selecting a first soybean plant comprising a genotype in the chromosome 3 genomic region flanked by loci FE704412 (SEQ ID NO: 1) and AW760852 (SEQ ID NO: 36) that is associated with a chloride tolerant phenotype from a population of soybean plants that is segregating for the genotype; and, b) crossing the selected soybean plant with a second soybean plant. In certain embodiments of these methods, one or both of the soybean plants comprises a transgene that confers glyphosate tolerance.

Further areas of applicability will become apparent from the description provided herein. It should be understood that the description and specific examples are intended for purposes of illustration only and are not intended to limit the scope of the present disclosure.

DETAILED DESCRIPTION OF INVENTION

I. Definition

As used herein, an "allele" refers to one of two or more alternative forms of a genomic sequence at a given locus on a chromosome. When all the alleles present at a given locus on a chromosome are the same, that plant is homozygous at that locus. If the alleles present at a given locus on a chromosome differ, that plant is heterozygous at that locus.

As used herein, the term "denoting" when used in reference to a plant genotype refers to any method whereby a plant is indicated to have a certain genotype. Such indications of a certain genotype include, but are not limited to, any method where a plant is physically marked or tagged. Physical markings or tags that can be used include, but not limited to, a barcode, a radio-frequency identification (RFID), a label or the like. Indications of a certain genotype also include, but are not limited to, any entry into any type of written or electronic database whereby the plant's genotype is provided.

A "locus" is a position on a genomic sequence that is usually found by a point of reference; e.g., a short DNA sequence that is a gene, or part of a gene or intergenic region. A locus may refer to a nucleotide position at a reference point on a chromosome, such as a position from the end of the chromosome.

As used herein, "linkage group N" corresponds to the soybean chromosome 3 described in Choi, et al., Genetics. 2007 May; 176(1): 685-696. Linkage group N, as used herein, also corresponds to soybean chromosome 19 (as described on the World Wide Web at soybase.org/LG2Xsome.php).

As used herein, "polymorphism" means the presence of one or more variations of a nucleic acid sequence at one or more loci in a population of at least two members. The variation can comprise but is not limited to one or more nucleotide base substitutions, the insertion of one or more nucleotides, a nucleotide sequence inversion, and/or the deletion of one or more nucleotides.

As used herein, the term "single nucleotide polymorphism," also referred to by the abbreviation "SNP," means a polymorphism at a single site wherein the polymorphism constitutes any or all of a single base pair change, an insertion of one or more base pairs, and/or a deletion of one or more base pairs.

As used herein, "marker" means a detectable characteristic that can be used to discriminate between organisms. Examples of such characteristics include, but are not limited to, genetic markers, biochemical markers, fermentation yield, fermentation efficiency, energy yield, secondary compounds, metabolites, morphological characteristics, and agronomic characteristics.

As used herein, "marker assay" means a method for detecting a polymorphism at a particular locus using a particular method. Marker assays thus include, but are not limited to, measurement of at least one phenotype (such as seed color, flower color, or other visually detectable trait as well as any biochemical trait), restriction fragment length polymorphism (RFLP), single base extension, electrophoresis, sequence alignment, allelic specific oligonucleotide hybridization (ASO), random amplified polymorphic DNA (RAPD), microarray-based polymorphism detection technologies, and the like.

As used herein, "genotype" means the genetic component of the phenotype and it can be indirectly characterized using markers or directly characterized by nucleic acid sequencing.

As used herein, the term "introgressed", when used in reference to a genetic locus, refers to a genetic locus that has been introduced into a new genetic background. Introgression of a genetic locus can thus be achieved through both plant breeding methods or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion. In certain embodiments, introgression could thus be achieved by substitution of a chloride intolerant locus with a corresponding chloride tolerant locus or by conversion of a locus from a chloride intolerant genotype to a chloride tolerant genotype.

As used herein, "phenotype" means the detectable characteristics of a cell or organism which can be influenced by gene expression.

As used herein, "linkage" refers to relative frequency at which types of gametes are produced in a cross. For example, if locus A has genes "A" or "a" and locus B has genes "B" or "b" and a cross between parent 1 with AABB and parent 2 with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, the termed "linked", when used in the context of markers and/or genomic regions, means that the markers and/or genomic regions are located on the same linkage group or chromosome.

As used herein, a "nucleic acid molecule," be it a naturally occurring molecule or otherwise may be "substantially purified", if desired, referring to a molecule separated from substantially all other molecules normally associated with it in its native state. More preferably, a substantially purified molecule is the predominant species present in a preparation. A substantially purified molecule may be at least about 60% free, preferably at least about 75% free, more preferably at least about 90% free, and most preferably at least about 95% free from the other molecules (exclusive of solvent) present in the natural mixture. The term "substantially purified" is not intended to encompass molecules present in their native state.

As used herein, "quantitative trait locus (QTL)" means a locus that controls numerically representable traits that are usually continuously distributed.

As used herein, the term "transgene" means nucleic acid molecules in the form of DNA, such as cDNA or genomic DNA, and RNA, such as mRNA or microRNA, which may be single or double stranded.

As used herein, the term "event", when used in the context of describing a transgenic plant, refers to a particular transformed plant line. In a typical transgenic breeding program, a transformation construct responsible for a trait is introduced into the genome via a transformation method. Numerous independent transformants (events) are usually generated for each construct. These events are evaluated to select those with superior performance.

As used herein, the term "soybean" means *Glycine max* and includes all plant varieties that can be bred with soybean, including wild soybean species. In certain embodiments, soybean plants from the species *Glycine max* and the subspecies *Glycine max* L. ssp. *max* or *Glycine max* ssp. *formosana* can be genotyped using the compositions and methods of the present invention. In an additional aspect, the soybean plant is from the species *Glycine soja*, otherwise known as wild soybean, can be genotyped using these compositions and methods. Alternatively, soybean germplasm derived from any of *Glycine max, Glycine max* L. ssp. *max, Glycine max* ssp. *Formosana*, and/or *Glycine soja* can be genotyped using compositions and methods provided herein.

As used herein, the term "bulk" refers to a method of managing a segregating population during inbreeding that involves growing the population in a bulk plot, harvesting the self pollinated seed of plants in bulk, and using a sample of the bulk to plant the next generation As used herein, the term "comprising" means "including but not limited to".

II. Description of the Invention: Overview

In accordance with the present invention, Applicants have discovered genomic regions, associated markers, and associated methods for identifying and associating genotypes that effect chloride tolerance. For example, in one embodiment, a method of the invention comprises screening a plurality of transgenic germplasm entries displaying a heritable variation for at least one chloride tolerance trait wherein the heritable variation is linked to at least one genotype; and associating at least one genotype from the transgenic germplasm entries to at least one chloride tolerance trait. In another embodiment, a method of the invention comprises crossing at least two germplasm entries with a test germplasm entry for the evaluation of performance of at least one chloride tolerance trait in order to determine preferred crossing schemes. The methods of the present invention can be used with traditional breeding techniques as described below to more efficiently screen and identify genotypes affecting a chloride tolerance trait.

The use of markers to infer a phenotype of interest results in the economization of a breeding program by substituting costly, time-intensive phenotyping assays with genotyping assays. Further, breeding programs can be designed to explicitly drive the frequency of specific, favorable phenotypes by targeting particular genotypes (U.S. Pat. No. 6,399,855). Fidelity of these associations may be monitored continuously to ensure maintained predictive ability and, thus, informed breeding decisions (US Patent Application 2005/0015827). In this case, costly, time-intensive phenotyping assays required for determining if a plant or plants contains a genomic region associated with a "chloride tolerant" or "chloride intolerant" phenotype can be supplanted by genotypic assays that provide for identification of a plant or plants that contain the desired genomic region.

III. A Genomic Region Associated with a Chloride Tolerant Phenotype

Provided herewith is a soybean genomic region that is shown herein to be associated with a desirable chloride tolerant phenotype when present in certain allelic forms and when combined with certain transgenic loci.

A soybean genomic region provided that can be associated with a desirable chloride tolerant phenotype when present in certain allelic forms is located on the telomere proximal end of the short arm of soybean chromosome 3 (linkage group N). A series of markers useful in practicing the methods of this invention are provided herein in Table 1. Additional markers useful in the practice of the invention are provided herein and in the priority document, the entirety of which is incorporated herein by reference. Table 4 provides the Table 1 markers with the relative positions of the markers on a physical map of chromosome 3 (linkage group N).

TABLE 1

Markers spanning a genomic region associated with a desirable chloride tolerant phenotype.

| Marker or Locus Name | SEQ ID NO: | Map Position [1] | Allelic form(s) Associated with Salt tolerant Phenotype [2] |
|---|---|---|---|
| FE704412 | 1 | 39551106 | |
| BI972982 | 2 | 39560541 | |
| NS0124217 | 3 | | AA[3] |
| NGMAX006180041 | 4 | 39583653 | |
| NGMAX006180060 | 5 | | |
| NGMAX006182912 | 6 | 40240411 | |
| NS0206277 | 7 | 40240411 | |
| NS0096117 | 8 | 40304796 | AA[4] |
| NGMAX008341275 | 9 | 40324148 | |
| NGMAX006182992 | 10 | 40371405 | |
| BG047538 | 11 | 40371824 | |
| NGMAX006183063 | 12 | 40382275 | |
| NS0205902 | 13 | 40462507 | TT[5] |
| NGMAX006183397 | 14 | 40470154 | |
| NS0262793 | 15 | | |
| NGMAX006183445 | 16 | 40484053 | |
| BI699634 | 17 | 40493363 | |
| NGMAX006183501 | 18 | 40498170 | |
| NGMAX006183536 | 19 | 40516416 | |
| NGMAX006183624 | 20 | 40536381 | |
| NGMAX006183651 | 21 | 40552979 | |
| NGMAX006183735 | 22 | 40569506 | |
| NGMAX006183784 | 23 | 40583780 | |
| NS0262794 | 24 | | |
| NGMAX006183900 | 25 | 40602686 | |
| NGMAX008341277 | 26 | 40618350 | |
| NGMAX006184117 | 27 | 40633921 | |
| NGMAX006184138 | 28 | 40645818 | |
| NGMAX006184179 | 29 | 40661090 | |
| NS0205793 | 30 | 40678452 | |
| NS0203171 | 31 | 40682526 | GG[6] |
| NGMAX006184354 | 32 | 40694726 | |
| NGMAX006184420 | 33 | 40701547 | |

TABLE 1-continued

Markers spanning a genomic region associated
with a desirable chloride tolerant phenotype.

| Marker or Locus Name | SEQ ID NO: | Map Position [1] | Allelic form(s) Associated with Salt tolerant Phenotype [2] |
|---|---|---|---|
| NGMAX006184463 | 34 | 40708067 | |
| AW719859 | 35 | 40714625 | |
| AW760852 | 36 | 40761388 | |

[1] The relative positions of the middle position of the listed markers or loci based on nucleotide positions on a physical map of soybean chromosome 3 (linkage group N) of Table 4 are provided where nucleotide position 39546539 is telomere proximal and nucleotide position 40761293 is centromere proximal. Polymorphic nucleotide bases are designated in the sequence listing provided herewith according to the WIPO Standard ST.25 (1998), Table 1, as follows: r = g or a (purine); y = t/u or c (pyrimidine); m = a or c; (amino); k = g or t/u (keto); s = g or c (strong interactions 3 H-bonds); w = a or t/u (weak interactions 2H-bonds); b = g or c or t/u (not a); d = a or g or t/u (not c); h = a or c or t/u (not g); v = a or g or c (not t, not u); and n = a or g or c or t/u (unknown, or other; any.)
[2] Both the maternal and paternal alleles of the single nucleotide polymorphisms that can be associated with a chloride tolerant phenotype are shown.
[3] The identified polymorphic allele of marker NS0124217 is located at nucleotide 172 of SEQ ID NO: 3.
[4] The identified polymorphic allele of marker NS0096117 is located at nucleotide 378 of SEQ ID NO: 8.
[5] The identified polymorphic allele of marker NS0205902 is located at nucleotide 128 of SEQ ID NO: 13.
[6] The identified polymorphic allele of marker NS0203171 is located at nucleotide 149 of SEQ ID NO: 31.

Also provided herein are sub-regions of the chromosome 3 region that is flanked by loci FE704412 (SEQ ID NO: 1) and AW760852 (SEQ ID NO: 36) that are associated with a salt tolerant phenotype. A first sub-region of the chromosome 3 region associated with a salt tolerant phenotype is flanked by loci BI1972982 (SEQ ID NO: 2) and BI699634 (SEQ ID NO: 17). These loci flank a first sub-region that spans telomere proximal nucleotide 39560541 to centromere proximal nucleotide 40462507 in the physical map of chromosome 3. Polymorphisms located in this first sub-region that are associated with a salt tolerant phenotype can be detected with markers that include, but are not limited to, NS0124217 (SEQ ID NO: 3), NS0096117 (SEQ ID NO: 8), NS0205902 (SEQ ID NO: 13), and NS0203171 (SEQ ID NO: 31). A second sub-region of the chromosome 3 region associated with a salt tolerant phenotype is flanked by loci BG047538 (SEQ ID NO: 11) and AW719859 (SEQ ID NO: 35). These loci flank the second sub-region that spans telomere proximal nucleotide 40371824 to centromere proximal nucleotide 40714625 in the physical map of chromosome 3. Polymorphisms located in this second sub-region that are associated with a salt tolerant phenotype can be detected with markers that include, but are not limited to, NS0205902 (SEQ ID NO: 13), and NS0203171 (SEQ ID NO: 31). In certain embodiments of invention, a polymorphism associated with a chloride tolerant phenotype is detected in only one of these sub-regions. In other embodiments of the invention, at least one polymorphism associated with a chloride tolerant phenotype is detected in both of these sub-regions.

Additional genetic markers can be used either in conjunction with the markers provided in Table 1 and/or Table 4 or independently of the markers provided in Table 1 and/or Table 4 to practice the methods of the instant invention. Publicly available marker databases from which useful markers can be obtained include, but are not limited to, the soybase.org website on the internet (World Wide Web) that is administered by the United States Agricultural Research Service, the United States Department of Agriculture, and Iowa State University. Additional soybean markers that can be used and that have been described in the literature include, but are not limited to, Hyten et al., *BMC Genomics*. 11:38, 2010; Choi et al., *Genetics*. 176(1):685-96, 2007; Yoon et al., *Theor Appl Genet*. 2007 March; 114(5):885-99; and Hyten et al. *Crop Sci.* 2010 50: 960-968. Given the provision herein of a genomic region on chromosome 3 (chromosome N) delimited or flanked by the telomere proximal locus FE704412 (SEQ ID NO: 1) of Table 2 and the centromere proximal locus AW760852 (SEQ ID NO: 36) of Table 2 as well as an assortment of soybean germplasms exhibiting either a "intolerant" or "salt tolerant" phenotype, additional markers located either within or near this genomic region that are associated with these phenotypes can be obtained by merely typing the new markers in the various germplasms provided herein. The genomic region on chromosome 3 delimited or flanked by the telomere proximal locus FE704412 (SEQ ID NO: 1) of Table 4 and the centromere proximal locus AW760852 (SEQ ID NO: 36) of Table 4 can also be mapped relative to markers provided in any publicly available or other soybean physical or genetic map to place this genetic locus on that map.

IV. Introgression of a Genomic Region Associated with a Salt Tolerant Phenotype

Also provided herein are unique soybean germplasm comprising an introgressed genomic region that is associated with a salt tolerant phenotype and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (i.e. such as a salt tolerant germplasm) and both linked and unlinked markers characteristic of the desired genetic background of a second germplasm (i.e. a salt intolerant germplasm). In addition to the markers provided herein that identify alleles of genomic region that is associated with a salt tolerant phenotype, flanking markers that fall on both the telomere proximal end of the genomic region on chromosome 3 (linkage group N) and the centromere proximal end of the chromosome 3 (linkage group N) genomic region are also provided in Tables 1 and 4. Such flanking markers are useful in a variety of breeding efforts that include, but are not limited to, introgression of the genomic region associated with a salt tolerant phenotype into a genetic background comprising markers associated with germplasm that ordinarily contains the allelic forms of the genomic region that is associated with a "salt tolerant" phenotype. Telomere proximal flanking markers that can be used in these methods include, but are not limited to, any of the loci listed in Table 4. Such polymorphisms can be identified by sequencing loci from chloride tolerant and chloride intolerant germplasms. Centromere proximal flanking markers that can be used in these methods include, but are not limited to, NS0124217 (SEQ ID NO: 3), NS0096117 (SEQ ID NO:8), NS0205902 (SEQ ID NO: 13), and NS0203171 (SEQ ID NO: 31). Publicly available marker databases from which additional useful markers located on chromosome 3 (linkage group N) and other chromosomes can be obtained include, but are not limited to, the soybase.org website on the internet that is administered by the United States Agricultural Research Service, the United States Department of Agriculture, and Iowa State University. Soybean plants or germplasm comprising an introgressed genomic region that is associated with a salt tolerant phenotype wherein at least 10%, 25%, 50%, 75%, 90%, or 99% of the remain genomic sequences carry markers characteristic of soybean plants or germplasm that are otherwise or ordinarily comprise a genomic region associated with the salt tolerant phenotype are thus provided.

In certain embodiments, the soybean plants provided herein or used in the methods provided herein can comprise a transgene that confers tolerance to glyphosate. Transgenes that can confer tolerance to glyphosate include, but are not limited to, transgenes that encode glyphosate tolerant Class I EPSPS (5-enolpyruvylshikimate-3-phosphate synthases) enzymes or glyphosate tolerant Class II EPSPS (5-enolpyruvylshikimate-3-phosphate synthases) enzymes. Useful glyphosate tolerant EPSPS enzymes provided herein are disclosed in U.S. Pat. Nos. 6,803,501, RE39,247, 6,225,114, 5,188,642, and 4,971,908. In certain embodiments, the glyphosate tolerant soybean plants can comprise a transgene encoding a glyphosate oxidoreductase or other enzyme which degrades glyphosate. Glyphosate oxidoreductase enzymes are described in U.S. Pat. No. 5,776,760 and U.S. Reissue Pat. RE38,825. In certain embodiments the soybean plant can comprise a transgene encoding a glyphosate N-acetyltransferase gene that confers tolerance to glyphosate. In certain embodiments, the soybean plant can comprise a glyphosate n-acetyltransferase encoding transgene, as described in U.S. Pat. No. 7,666,644. In still other embodiments, soybean plants comprising combinations of transgenes that confer glyphosate tolerance are provided. Soybean plants comprising both a glyphosate resistant EPSPS and a glyphosate N-acetyltransferase are also provided herein. In certain embodiments, it is contemplated that the soybean plants used herein can comprise one or more specific genomic insertion(s) of a glyphosate tolerant transgene including, but not limited to, those found in: i) MON89788 soybean (deposited under ATCC accession number PTA-6708 and described in US Patent Application Publication Number 20100099859), ii) GTS 40-3-2 soybean (Padgette et al., Crop Sci. 35: 1451-1461, 1995), iii) event 3560.4.3.5 soybean (seed deposited under ATCC accession number PTA-8287 and described in US Patent Application Publication Number 20090036308), or any combination of i (MON89788 soybean), ii (GTS 40-3-2 soybean), and iii (event 3560.4.3.5 soybean).

In certain embodiments, it is contemplated that genotypic assays that provide for non-destructive identification of the plant or plants can be performed either in seed, the emergence stage, the VC stage (i.e. cotyledons unfolded), the V1 stage (appearance of first node and unifoliate leaves), the V2 stage (appearance of the first trifoliate leaf), and thereafter. In certain embodiments, non-destructive genotypic assays are performed in seed using apparati and associated methods as described in U.S. Pat. Nos. 6,959,617; 7,134,351; 7,454,989; 7,502,113; 7,591,101; 7,611,842; and 7,685,768, which are incorporated herein by reference in their entireties. In certain embodiments, non-destructive genotypic assays are performed in seed using apparati and associated methods as described in US Patent Application Publication Nos. 20100086963, 20090215060, and 20090025288, which are incorporated herein by reference in their entireties. Published U.S. Patent Application Nos. 2006/0042527, 2006/0046244, 2006/0046264, 2006/0048247, 2006/0048248, 2007/0204366, and 2007/0207485, which are incorporated herein by reference in their entirety, also disclose apparati and systems for the automated sampling of seeds as well as methods of sampling, testing and bulking seeds. Thus, in certain embodiments, any of the methods provided herein can comprise screening for markers in individual seeds of a population wherein only seed with at least one genotype of interest is advanced.

V. Molecular Assisted Breeding Techniques

Genetic markers that can be used in the practice of the instant invention include, but are not limited to, Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (US Patent Application Publication Numbers 2005/0204780, 2005/0216545, 2005/0218305, and 2006/00504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis.

As a set, polymorphic markers serve as a useful tool for fingerprinting plants to inform the degree of identity of lines or varieties (U.S. Pat. No. 6,207,367). These markers form the basis for determining associations with phenotype and can be used to drive genetic gain. The implementation of marker-assisted selection is dependent on the ability to detect underlying genetic differences between individuals.

Certain genetic markers for use in the present invention include "dominant" or "codominant" markers. "Codomninant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

Markers that include, but are not limited to, single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with salt tolerant loci, regions flanking salt tolerant loci, regions linked to salt tolerant loci, and/or regions that are unlinked to salt tolerant loci can be used in certain embodiments of the instant invention.

Nucleic acid-based analyses for determining the presence or absence of the genetic polymorphism (i.e. for genotyping) can be used for the selection of seeds in a breeding population. A wide variety of genetic markers for the analysis of genetic polymorphisms are available and known to those of skill in the art. In certain embodiments of the instant invention, the aforementioned analyses may be used to select for genes, portions of genes, QTL, alleles, or genomic regions (genotypes) that comprise or are linked to a genetic marker that is linked to or correlated with salt tolerant loci, regions flanking salt tolerant loci, regions linked to salt tolerant loci, and/or regions that are unlinked to salt tolerant loci.

Herein, nucleic acid analysis methods include, but are not limited to, PCR-based detection methods (for example, TaqMan assays), microarray methods, mass spectrometry-based methods and/or nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent No. 50,424; European Patent No. 84,796; European Patent No. 258,017; European Patent No. 237,362; European Patent No. 201,184; U.S. Pat. Nos. 4,683,202; 4,582,788; and 4,683,194), using primer pairs that are capable of hybridizing to the proximal sequences that define a polymorphism in its double-stranded form.

Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252, all of which are incorporated herein by reference in their entireties. However, the compositions and methods of the present invention can be used in conjunction with any polymorphism typing method to type polymorphisms in genomic DNA samples. These genomic DNA samples may include, but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane, and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group, which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer), which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated, and thus, only one of the two labels will be detected. Heterozygous samples have both alleles present, and will thus directly incorporate both labels (into different molecules of the extension primer), thereforeboth labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle, DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (lincoln, NE), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTL, particularly in the case of genotypes.

EXAMPLES

The following examples are included to demonstrate preferred embodiments of the invention. It should be appreciated by those of skill in the art that the techniques disclosed in the following examples represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Identification of a Locus Associated with Salt Tolerance

Data collected using the described phenotypic method was used for an association study. Data included 294 soybean lines with maturity ranges from which ranged from 4.0-6.9. These entries were scored on a 1-5 scale and then converted to a 1-9 scale for reporting. The results of the study confirmed the location of one major QTL on chromosome 6 (linkage group N). The data in the association study was evaluated using two statistical methods: Maximum likelihood interval mapping (ML_IM) and Bayesian multi-marker mapping (Bayes_MM). Both of these methods show on major peak (LOD score>30), in the same location.

Example 2. Phenotyping Chloride Tolerance

Plants are phenotyped in a tub with drilled holes a cap mat liner and a 1.5-2 inch sand base. A thin layer of vermiculite is added to just cover the sand. 15 1-inch rings of PVC piping are pushed into the media. Label tags are placed in each well for identification and fifteen (15) seeds are placed on the vermiculite layer. Plants are scored approximately fifteen (15) days after the first addition of salt. Plants are then moved to an automated watering system. Salt water (EC— 7.5 d/S/m) is added by flooding every other day. Plants are grown in a greenhouse or growth chamber and watered normally for ten (10) days. PVP pipe is then filled with another layer of vermiculite to cover seeds. Individual plants are rated on a 1-5 scale, which is subsequently converted to a 1-9 scale for reporting. Visual rating is based both on chlorosis and necrosis. Only trifolates are considered in the rating. Individual ratings are averaged across each line.

Example 3. Exemplary Marker Assays for Detecting Polymorphisms

In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. Exemplary primers and probes for amplifying and detecting genomic regions associated with a salt tolerant phenotype are given in Table 2.

TABLE 2

Exemplary Assays for Detecting Polymorphisms

| Marker or Locus Name | Marker SEQ ID | SNP Position | SEQ ID Forward Primer | SEQ ID Reverse Primer | SEQ ID Probe 1 | SEQ ID Probe 2 |
|---|---|---|---|---|---|---|
| NS0124217 | 3 | 172 | 37 | 38 | 39 | 40 |
| NS0096117 | 8 | 378 | 41 | 42 | 43 | 44 |
| NS0205902 | 13 | 128 | 45 | 46 | 47 | 48 |
| NS0203171 | 31 | 111.6 | 49 | 50 | 51 | 52 |

Example 4: Oligonucleotide Probes Useful for Detecting Polymorphisms by Single Base Extension Methods Oligonucleotides can also be used to detect or type the polymorphisms disclosed herein by single base extension (SBE)-based SNP detection methods. Exemplary oligonucleotides for use in SBE-based SNP detection are provided in Table 3. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in Table 4 in the columns labeled "Forward Primer SEQ ID" and "Reverse Primer SEQ ID". Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus directly incorporate both labels (into different molecules of the extension primer), thereforeboth labels will be detected. Exemplary forward and reverse SBE probes are provided in Table 3.

TABLE 3

Exemplary SBE Probes for Detecting Polymorphisms

| Marker or Locus Name | Marker SEQ ID NO: | SNP Position | Probe (SBE) | Probe (SEQ ID NO.) |
|---|---|---|---|---|
| NS0124217 | 3 | 172 | AACCTCACAATGCAGTCT | 39 |
| NS0096117 | 8 | 378 | CCCCAAAAAATAAAA | 43 |
| NS0205902 | 13 | 128 | TTGATGGGTAGTAGGTTGTG | 47 |
| NS0203171 | 31 | 111.6 | AGCTCTTGATTGGTTTTG | 51 |

TABLE 4

Chloride Tolerant Genomic Region on Chromosome 3 (Linkage Group N)

| Locus/ DisplayName | SEQ ID NO: | Source | Start Position | Stop Position | Additional Information |
|---|---|---|---|---|---|
| FE704412 | 1 | Phaseolus_vulgaris | 39546539 | 39555673 | UniRef100_O81117 Cytochrome P450 94A1 n = 1 Tax = Vicia sativa RepID = C94A1_VICSA 1.00E−88 |
| BI972982 | 2 | Glycine_max_release_2 | 39560285 | 39560798 | NA |
| NS0124217 | 3 | | 39579678 | 39580847 | |
| NGMAX006180041 | 4 | | 39583503 | 39583804 | |
| NGMAX006180060 | 5 | | 39628183 | 39628484 | |
| NGMAX006182912 | 6 | | 40240068 | 40240755 | |
| NS0206277 | 7 | | 40240068 | 40240755 | |
| NS0096117 | 8 | | 40304441 | 40305151 | |
| NGMAX008341275 | 9 | | 40323998 | 40324299 | |
| NGMAX006182992 | 10 | | 40371255 | 40371556 | |
| BG047538 | 11 | Glycine_soja_release_2 | 40371654 | 40371994 | NA |
| NGMAX006183063 | 12 | | 40382125 | 40382426 | |
| NS0205902 | 13 | | 40462307 | 40462708 | |
| NGMAX006183397 | 14 | | 40470004 | 40470305 | |
| NS0262793 | 15 | | | | |
| NGMAX006183445 | 16 | | 40483903 | 40484204 | |
| BI699634 | 17 | Glycine_max_release_2 | 40490936 | 40495791 | HEAT [Medicago truncatula (Barrel medic)] |
| NGMAX006183501 | 18 | | 40498020 | 40498321 | |
| NGMAX006183536 | 19 | | 40516266 | 40516567 | |
| NGMAX006183624 | 20 | | 40536231 | 40536532 | |
| NGMAX006183651 | 21 | | 40552829 | 40553130 | |
| NGMAX006183735 | 22 | | 40569356 | 40569657 | |
| NGMAX006183784 | 23 | | 40583630 | 40583931 | |
| NS0262794 | 24 | | | | |
| NGMAX006183900 | 25 | | 40602536 | 40602837 | |
| NGMAX008341277 | 26 | | 40618200 | 40618501 | |
| NGMAX006184117 | 27 | | 40633771 | 40634072 | |
| NGMAX006184138 | 28 | | 40645668 | 40645969 | |
| NGMAX006184179 | 29 | | 40660940 | 40661241 | |
| NS0205793 | 30 | | 40678642 | 40678262 | |
| NS0203171 | 31 | | 40682708 | 40682344 | |
| NGMAX006184354 | 32 | | 40694576 | 40694877 | |
| NGMAX006184420 | 33 | | 40701397 | 40701698 | |
| NGMAX006184463 | 34 | | 40707917 | 40708218 | |
| AW719859 | 35 | Lotus_japonicus_release_1 | 40714008 | 40715242 | Peptidase M14, carboxypeptidase A [Medicago truncatula (Barrel medic)] |
| AW760852 | 36 | Glycine_max_release_2 | 40760783 | 40761994 | Diaminopimelate epimerase-like protein [Arabidopsis thaliana (Mouse-ear cress)] |

Example 5. Using Markers to Select Alleles Associated with Salt Tolerance

Greenhouse studies demonstrate that using markers to screen soybean varieties for salt tolerance is an effective means to select plants with the desired salt tolerance phenotype. Plants are grown in a greenhouse under high salt conditions and phenotyped as described in Example 2. A Chloride Reaction in the Greenhouse (CLGH) rating (1-9 scale) is assigned to plants, indicating the percentage of chlorosis/necrosis exhibited by a plant under the stressed conditions. In one embodiment, soybean varieties comprising a TT allele of marker NS0205902 (SEQ ID NO: 13) have an average CLGH rating of 1.7, indicating tolerance to high salt conditions; whereas varieties comprising a GG allele of NS0205902 (SEQ ID NO: 13) have an average CLGH rating of 5.3, indicating intolerance to high salt conditions. In another embodiment, soybean varieties comprising a GG allele of marker NS0203171 (SEQ ID NO: 31) have an average CLGH rating of 1.8, indicating a tolerance to high salt conditions; whereas varieties comprising a CC allele of NS0203171 have an average CLGH rating of 5.2, indicating intolerance to high salt conditions.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

We claim:

1. A method for obtaining a soybean plant comprising in its genome at least one chloride tolerance locus, the method comprising the steps of:
producing a plurality of soybean plants by crossing a parent plant comprising at least one chloride tolerance locus with a parent plant comprising at least one chloride sensitivity locus;
genotyping said plurality of soybean plants with respect to at least one genetic locus associated with chloride tolerance, wherein the genetic locus is on chromosome 3 and is flanked by loci NGMAX006180041 (SEQ ID NO:4) and NGMAX006184463 (SEQ ID NO:34); and
selecting a soybean plant comprising in its genome at least one genetic locus comprising a genotype associated with chloride tolerance, wherein said genotype associated with chloride tolerance comprises at least one polymorphic allele of NS0203171 (SEQ ID NO:31).

2. The method of claim 1, wherein said marker comprises a GG allele of NS0203171 (SEQ ID NO: 31).

* * * * *